(12) United States Patent
Hummel et al.

(10) Patent No.: US 10,792,633 B2
(45) Date of Patent: Oct. 6, 2020

(54) COMPOSITION COMPRISING A FLUORINE-CONTAINING SURFACTANT

(71) Applicant: HWK-Kronbichler GmbH, Ebbs (AT)

(72) Inventors: Michael Hummel, Innsbruck (AT); Benjamin Naier, Innsbruck (AT); Herwig Schottenberger, Patsch (AT); Hubert Huppertz, Innsbruck (AT); Gabriel Partl, Fliess (AT); Michael Noisternig, Nassereith (AT)

(73) Assignee: HWK-KRONBICHLER GMBH, Ebbs (AT)

( * ) Notice: Subject to any disclaimer, the term of this patent is extended or adjusted under 35 U.S.C. 154(b) by 0 days.

(21) Appl. No.: 16/078,721

(22) PCT Filed: Feb. 24, 2017

(86) PCT No.: PCT/EP2017/000262
§ 371 (c)(1),
(2) Date: Aug. 22, 2018

(87) PCT Pub. No.: WO2017/144181
PCT Pub. Date: Aug. 31, 2017

(65) Prior Publication Data
US 2019/0060858 A1 Feb. 28, 2019

(30) Foreign Application Priority Data
Feb. 25, 2016 (EP) .................... 16157380

(51) Int. Cl.
*B01F 1/00* (2006.01)
*B01F 17/00* (2006.01)
(Continued)

(52) U.S. Cl.
CPC ...... *B01F 17/0057* (2013.01); *B01F 17/0035* (2013.01); *B01F 17/0042* (2013.01);
(Continued)

(58) Field of Classification Search
CPC ............. B01F 17/0035; B01F 17/0042; B01F 17/0057; C11D 3/3776; C11D 3/378; C11D 3/3773; C11D 1/62; C11D 1/143
See application file for complete search history.

(56) References Cited

U.S. PATENT DOCUMENTS 3,933,819 A * 1/1976 Toukan ................. C07C 323/00
544/315
4,042,522 A * 8/1977 Falk ..................... C07D 295/13
252/8.05

(Continued)

FOREIGN PATENT DOCUMENTS

DE 1966931 A1 5/1975
WO 2011046796 A1 4/2011

OTHER PUBLICATIONS

International Search Report and Written Opinion (with English translation of International Search Report) issued in corresponding International Patent Application No. PCT/EP2017/000262 dated May 23, 2017 (15 pages).

(Continued)

*Primary Examiner* — John R Hardee
(74) *Attorney, Agent, or Firm* — Kilyk & Bowersox, P.L.L.C.

(57) ABSTRACT

The invention relates to a composition comprising a fluorine-containing surfactant having a cationic group, a divalent sulfur-containing group and a fluorinated group, further comprising an anion that corresponds to the cationic group of the fluorine-containing surfactant, the cationic group being an N-alkylated heterocyclic group.

19 Claims, 5 Drawing Sheets

(51) Int. Cl.
  *C07D 233/84* (2006.01)
  *C07C 49/167* (2006.01)
  *C07F 9/17* (2006.01)
  *C07C 309/15* (2006.01)
  *C07C 309/12* (2006.01)

(52) U.S. Cl.
  CPC .......... *C07C 49/167* (2013.01); *C07C 309/12* (2013.01); *C07C 309/15* (2013.01); *C07D 233/84* (2013.01); *C07F 9/17* (2013.01)

(56) References Cited

U.S. PATENT DOCUMENTS

| | | |
|---|---|---|
| 4,242,516 A | 12/1980 | Mueller |
| 2015/0368182 A1 | 12/2015 | Johnson |

OTHER PUBLICATIONS

J. C. Barsigian, "Product Data Sheet", Eye Res. J. Biol. Chem, Jan. 1, 1998 (3 pages).

* cited by examiner

COMPOSITION COMPRISING A FLUORINE-CONTAINING SURFACTANT

This application is a National Stage Application of PCT/EP2017/000262, filed Feb. 24, 2017, which claims priority to European Patent Application No. 16157380.3 filed Feb. 25, 2016.

The invention relates to a composition comprising a surfactant containing fluorine and having a cationic group, a bivalent or polyvalent sulfurous group, and a fluorinated group and further comprising an anion corresponding to the cationic group of the surfactant containing fluorine.

Compounds containing fluorine are used as surfactants in a number of industrial branches. Possibilities of use include the staining of wood, the production and processing of fossil fuels in the oil and natural gas industry, the addition to polymerizable compositions, the use as non-flammable surfactants in extinguishing agents and in particular in foam, and the use in paints, printing inks, cleaning agents, adhesives, contact lenses, chalks, fabrics, textiles, polishes and waxes, on hard surfaces, in electronics and in metal coatings, as coupling agents or as lubricants. Some important tasks here include improving the progression, the effect as an emulsifying agent, reducing the "orange peel effect" and pinholing, improving the gloss, increasing oxygen solubility, the pot life, setting oleophobic and hydrophobic (amphiphobic) properties, monitoring the foam formation, the surface wetting, the UV stability and the weather resistance, or controlling the swelling behavior of hydrogels.

U.S. Pat. No. 4,062,849 A describes the use of cationic fluorine compounds as surfactants. Compounds of the formula shown below are described therein.

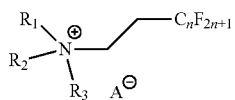

WO 2011/046796 A1 and EP 0 256 980 A2 also disclose cationic fluorosurfactants, inter alia those in according with the following formulas.

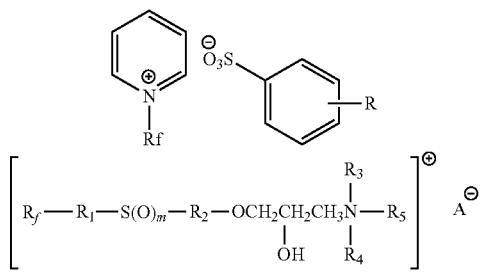

U.S. Pat. Nos. 3,513,172 A and 8,901,311 B2 disclose unloaded compounds containing fluorine of the structure shown in the following without reference to their possible use as surfactants.

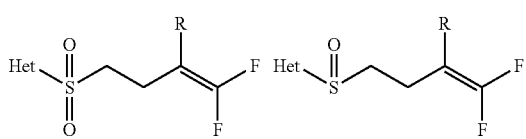

The use of these compounds for pest control is thought about in the application US 2006/0173190 A1.

It is the aim of the present invention to provide a composition having surfactants that contain fluorine, that have improved properties with respect to known surfactants containing fluorine, and that are easily accessible synthetically. The degradability and the environmental compatibility should also be improved in preferred embodiments.

Against this background, the invention relates to a composition comprising a surfactant containing fluorine and having a cationic group, a bivalent or polyvalent sulfurous group, and a fluorinated group and further comprising an anion corresponding to the cationic group of the surfactant containing fluorine, with the cationic group being an N-substituted group, and preferably an N-alkylated heterocyclic, and in particular heteroaromatic, group.

The compositions in accordance with the invention can be prepared substantially less expensively with respect to the compositions already known from, for example, U.S. Pat. No. 4,062,849 A and EP 0 256 980 A2 and the structure and thus the properties of the surfactants can be synthetically modified in a simple manner.

The fluorinated group comprises C—F bonds. A hydrophobic and oleophobic (amphiphobic) effect emanates from the fluorinated group. The cationic group enables the solution of the fluorosurfactants in solvents having a higher polarity and increases the interaction with substrates that have at least one negative partial charge. In addition, specific anions that in turn have an effect on the surface activity of the composition can also be introduced due to the cationic charge of the fluorosurfactants.

In an embodiment, the cationic group is an N,N-disubstituted and preferably N,N-dialkylated imidazol(in)ium group or a benzimidazol(in)ium group or a protonated N-substituted and preferably N-alkylated imidazol(in)ium group or benzimidazol(in)ium group.

In an embodiment, the surfactants comprise exactly one cationic group.

In an embodiment, the fluorinated group is a completely fluorinated hydrocarbon group. A completely fluorinated and optionally linear group of the type —$(CF_2)_n$—$CF_3$ is preferred, where n is between 2 and 9 and is preferably 4, 5, or 6. A completely fluorinated hydrocarbon group is to be understood as a perfluoroorganyl group in which all hydrogen atoms have been replaced with fluorine atoms. A total chain length of 5 to 7 fluorinated C atoms is particularly advantageous since the hydrophobic and oleophobic properties of the fluorosurfactants are already very highly pronounced with this chain length, but good environmental compatibility is simultaneously also present. The use of a perfluorohexyl group having the structural formula —$(CF_2)_5$—$CF_3$ is particularly preferred.

In an embodiment, the fluorinated chain can comprise a fluoroether. A synthesis of such ethers is described in Skalicky et al., Organometallics, 2012, 31 (4), pp 1524-1532.

In an embodiment, the surfactants comprise exactly one fluorinated group.

In an embodiment, the sulfurous group is a thioether or a sulfide bridge so that a thioether (an organylsulfide group) substituted at the cationic group is present in the surfactant. Alternative sulfurous groups include polysulfides, sulfides, disulfides, sulfoxides, and sulfones. Such a thioether can be obtained by substitution reaction from a thione group and, for example, from a halogenated hydrocarbon. In addition, they can be transformed into a sulfoxide group and a sulfonate group by targeted oxidation. A thione can furthermore also be transformed oxidatively into a disulfide that then likewise has a positive charge.

In an embodiment, the fluorosurfactants comprise exactly one sulfurous group.

In an embodiment, the anion is separately present in the composition; that is, it is not covalently bonded to the surfactant. Suitable anions include, for example, fluoride, chloride, bromide, iodide, aryl sulfonate, alkyl sulfonate, alkyl sulfate, sulfate, aryl phosphonate, alkyl phosphonate, monoalkyl phosphate, tetrafluoroborate, dialkyl phosphate, (di)hydrogen phosphate, phosphate, hexafluorophosphate, hydrogen carbonate, carbonate, carbamate, alkyl carbonate, trifluoromethanesulfonate, bis(trifluoromethane sulfonyl) imide, nonaflate, carboxylate, picrate, hennate or pyridoxal phosphate. In addition, hypergolic anions and/or complex metalates are conceivable.

In an embodiment, the anions are anions that occur in pharmaceutically acceptable salts. They are described, for example, in Haynes et al. Wiley InterScience 2005 and in Handbook of Pharmaceutical Salts Properties, Selection, and Use 2008 Helvetica Chimica Acta.

In an embodiment, the separately present anions represent a polymerizable compound that has a crosslinkable group and an anionic group. Suitable crosslinkable groups include ethylenic functionalities. Ally groups, propargyl groups, (meth)acrylate groups or (meth)acrylamide groups and/or substituted or unsubstituted vinyl groups are particularly preferred. Suitable anionic groups include the above-discussed groups provided that they can be covalently bonded to a hydrocarbon. Anions that are formed by splitting off an acidic proton are preferred here. Examples of suitable compounds comprise derivatives of the (meth)acrylate or (meth) acrylamide, for example derivatives of the (meth)acrylate or (meth)acrylamide that include at least one sulfate group, sulfonate group, phosphonate group, phosphate group, carbonate group, carbamate group, triflate group, or carboxylate group, in particular a sulfonate group. Non-limiting specific examples include 2-acrylamido-2-methylpropane sulfonate, 3-sulfopropyl(meth)acrylate, 3-sulfoethyl(meth) acrylate or 3-(acryloyloxy)-1-propane sulfonate. In an embodiment, the polymerizable anions can be present as an oligomer, prepolymer, polymer and/or a telechelic macronomer.

In an embodiment, the anion in turn has a fluorinated group that can, for example, be formed as has been described in connection with the fluorinated group of the surfactant. Such anions in turn have a surface-active effect. Suitable examples include substitutes of perfluorooctanoic acid (PFOA) or perfluorooctane sulfonate (PFOS) such as 3H-perfluoro-3-((3-methoxy-propoxy)propanoic acid) in an embodiment, the anion is represented by halogenides. Iodides and chlorides are particularly preferred.

In an embodiment, the composition further comprises an halogenoalkane, with the halogenoalkane preferably carrying a fluorinated group. The fluorinated group of the halogenoalkane can, for example, also be a partially or fully fluorinated hydrocarbon group, preferably a completely fluorinated linear group of the type —$(CF_2)_n$—$CF_3$, where n is between 2 and 10 and preferably between 4 and 8. The halogenoalkane can, for example, be of the type X—$(CH_2)_m$—$(CF_2)_n$—$CF_3$, where X is a halogen and is preferably bromine or iodine and m can be between 0 and 5 and is preferably 0 since the electronegativity of the fluorine atoms promotes the formation of a halogen complex. Preferred halogenoalkanes include 1-bromoperfluorooctane, 1-iodoperfluorooctane, or 1-iodoperfluorohexane. The halogenoalkane can form a so-called halogen complex with a halogenide anion and preferably an iodide atom, with a halogen complex being understood as a non-covalent interaction between a halogen and an interaction partner. A comprehensive description of these complexes can be found, for example, in Gilday et al., Chem. Rev. 2015, 115, 7118-7195. In addition to iodoalkanes, aromatic halogenated systems and nitrogenous compounds are described therein that can form such a complex. This already has a plurality of positive effects on the application. On the one hand, electron density is pulled off away from the cationic group of the fluorosurfactants due to the delocalization of the negative charge via the two halogen atoms of the complex, for example, which produces a higher positive charge and therefore an improved solubility of the functionalized monomers in an organic solvent having a higher polarity or a higher dipole moment. The hydrophobic and oleophobic effect of the fluorosurfactant can furthermore be increased by a functionalization of the halogenoalkane with a fluorinated group, without having to increase the chain length of the fluorinated group in the functionalized surfactants. Finally, the halogenoalkane can also serve as a reagent for further reactions in order, for example, to react with residues of a photoinitiator.

In an embodiment, the anion is a zwitterionic compound, preferably a betaine.

In an embodiment, the anion is formed by an anionic group covalently bonded to the surfactant containing fluorine. To this extent, the fluorinated surfactants can be betaines. Preferred anionic groups here include sulfate, sulfonate, phosphonate, phosphate, carbonate, trifluoromethanesulfonate, carbamate, triflate, or carboxylate, in particular sulfonate. Sulfonate anions can effect good solubility in water, for example.

In an embodiment, the composition comprises a combination of two or more different anions.

In an embodiment, the sulfurous group is arranged between the cationic group and the covalently bonded anionic group, with the covalently bonded anionic group being bonded to the sulfurous group directly or with an interposed spacer. The sulfurous group can here, for example, be directly bonded to the C2 of the cationic group.

In an embodiment, the covalently bonded anion is bonded to a nitrogen atom, for example to the N1 or N3 of the cationic group, with an interposed spacer.

In an embodiment, the fluorinated group is bonded to a nitrogen atom, for example to the N1 or N3 of the cationic group, directly or with an interposed spacer.

In an embodiment, the sulfurous group is arranged between the cationic group and the fluorinated group, with the fluorinated group being bonded to the sulfurous group directly or with an interposed spacer. The sulfurous group can here, for example, also be directly bonded to the C2 of the cationic group.

In an embodiment, the surfactant has a crosslinkable group so that a cross-linkable or polymerizable surfactant is produced. Suitable crosslinkable groups, for example, comprise those groups that have already been described in connection with the crosslinkable anions. They can, however, also be alcohols and amines that can, for example, be crosslinked with isocyanates.

In an embodiment, the crosslinkable group is substituted at a nitrogen atom, for example at the N1 or N3 of the cationic group, directly or with an interposed spacer.

In an embodiment, the sulfurous group is arranged between the cationic group and the crosslinkable group, with the crosslinkable group being bonded to the sulfurous group directly or with an interposed spacer. The sulfurous group can here, for example, also be directly bonded to the C2 of the cationic group.

In an embodiment, the spacer is a linear or branched C1-C10, preferably a C1-C5, and further preferably C2-C3, alkylene group, in particular ethylene. The spacer is preferably uncharged and/or non-fluorinated. Methylene or an alkylene having a maximum of C6 can also be used.

In an embodiment, the fluorosurfactant has the structure shown below, with n being defined as above.

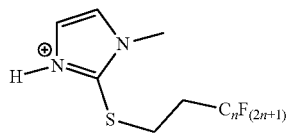

In an embodiment, the fluorinated surfactants have between 8 and 50 heavy atoms, and preferably between 10 and 30 heavy atoms. A heavy atom is understood as all atoms except for hydrogen in the present case.

In an embodiment, the surfactant containing fluorine has one of the following structures:

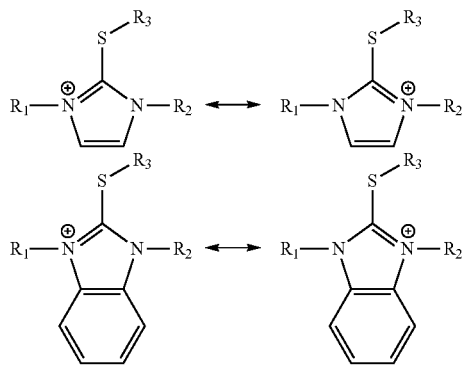

where one of the residues $R_1$, $R_2$ or $R_3$ represents a $(CH_2)_{1-5}(CF_2)_{3-10}CF_3$ group and the two further ones of the residues represent, independently of one another, hydrogen or a substituted or unsubstituted C1-C10 alkyl group that can optionally have a crosslinkable group (the alkyl group becomes the alkylene group from case to case here) or a covalently bonded anionic group. The alkyl group can here be linear or branched. Suitable substituted alkyl groups include alkoxy alkyls, aralkyls, haloalkyls, or alkyls having substitutes such as sulfonamide or N-oxide. Examples of suitable substituted alkyl groups include a $-(CH_2)_{1-10}-NH_2$, a $-(CH_2)_{1-10}-OH$ and a $(CH_2)_{1-10}SH$.

Provided that the surfactant has a crosslinkable group, the surfactant can also be present as an oligomer of covalently bonded units. Such oligomers can, for example, take place by reactions of alcohol or amines with isocyanates to form the corresponding urethanes or urea derivatives or by crosslinking of isocyanates or epoxides. In addition, thiols can, for example, be transformed into oligomers or polymers by means of a thiol-ene click reaction. Reactions with alkyl residues substituted at both ends are likewise conceivable. Examples of suitable dimers or multimers include the following, in a non-limiting manner:

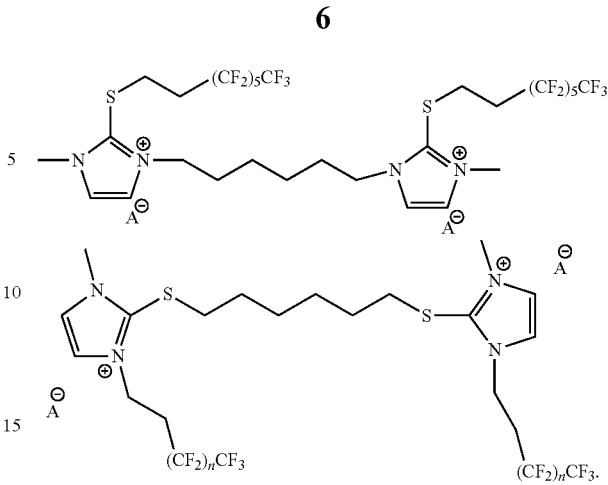

In an embodiment, the molar mass of the fluorinated surfactants is between 100 and 3500 g/mol, preferably between 130 and 1000 g/mol.

In an embodiment, the surfactant can be present in the composition by means of the crosslinkable group as a dimer, trimer, or oligomer.

In an embodiment, the composition can comprise further surfactants in addition to the named fluorinated surfactants.

In an embodiment, the fluorosuriactants used can be an ionic liquid that is preferably present as a liquid at 25° C. In the simplest case, the composition only consists of the functionalized surfactants in accordance with the invention.

In other embodiments, the surfactant is diluted with a suitable solvent for the respective application and is subsequently introduced into the composition provided for the respective application. The preferred solvent is water; however, other polar and apolar solvents or even ionic liquids are suitable as potential solvents.

In an embodiment, the composition comprises between 0.01 and 99.999% wt % water.

In an embodiment, the composition comprises between 0.001 and 100% wt % of the fluorinated surfactant.

The surfactants of the compositions in accordance with the invention have excellent solubility profiles and antistatic properties. They can be controlled in dependence on the application both by the selection of the substitutes, the design of the fluorine chain(s) (completely fluorinated chain, fluoroether as the chain, branched chain(s), chain length) and by the anion. There is therefore a high flexibility both in the synthesis and a wide possibility of use in the application.

Against the initially named background, the invention further relates to the use of the composition in accordance with the invention as a surface-active agent. A use is conceivable to reduce the surface tension, as a defoamer, for setting optical properties, or for setting the oxygen solubility or oxygen permeability. In an embodiment, the composition is used in surface coatings, lacquers, extinguishing agents, hydrogels and/or in the polymerization of fluoropolymers. Reference is further made to the applications named in the introductory part of the patent description.

The invention finally relates to a method of manufacturing the composition in accordance with the invention. Such a method can, for example, comprise the step of a conversion of an uncharged compound with an N-substituted and preferably N-alkylated heterocyclic group, with a bivalent or polyvalent sulfurous group, and a fluorinated group with an acid. Alternatively or additionally, a quaternization, metathesis or the like can be provided such as results from the description of the embodiments.

BRIEF DESCRIPTION OF THE DRAWINGS

Further details and advantages of the invention result from the embodiments inter alia described in the following with reference to the Figures. There are shown in the Figures.

Figure 1:
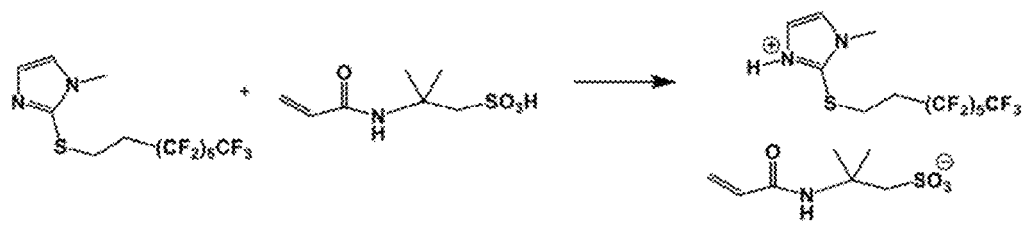
FIG. 1: a reaction equation for the synthesis of a polymerizable surfactant containing fluorine.

A compound containing fluorine that is preferred within the framework of the present invention, that acts as a surfactant, and that additionally comprises a crosslinkable functionality is shown in FIG. 1 with 2-acrylamido-2-methylpropanesulfonate as the counter-ion. The anion can be polymerized by the acrylamide functionality.

Figure 2:
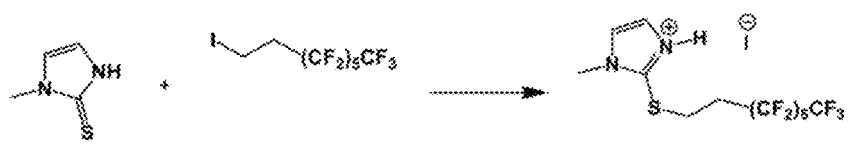
FIG. 2: a reaction equation for the synthesis of a surfactant containing fluorine from thiamazole.

FIG. 2 shows a reaction equation for the synthesis of a surfactant containing fluorine in accordance with the invention from thiamazole. This alkylation is successful with particularly good yields and is associated with low costs.

Figure 3:
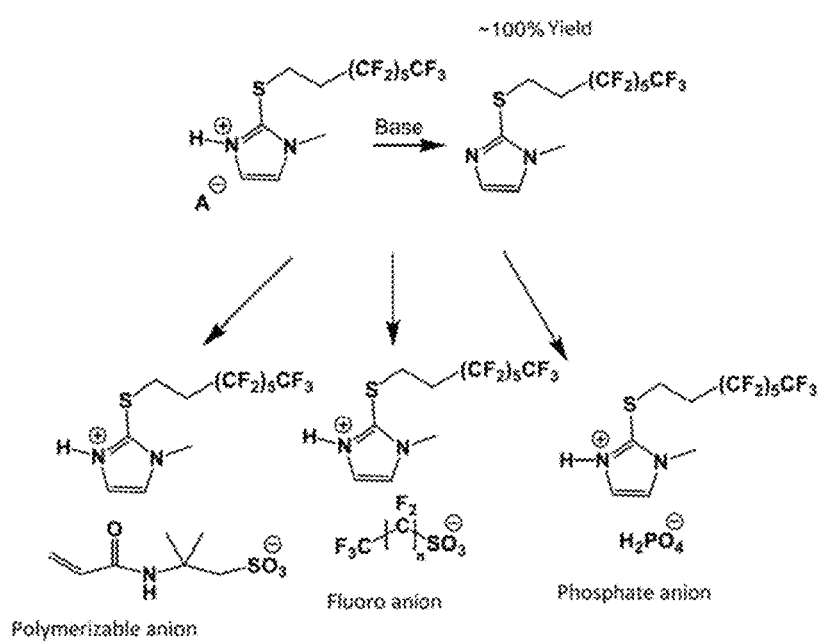
FIG. 3: a reaction equation for the synthesis of a surfactant containing fluorine from a fluorine base with an acid.

The reaction equation in accordance with FIG. 3 is representative for a generally synthetic access to surfactants containing fluorine in accordance with the invention. Starting from a surfactant containing fluorine in accordance with the invention, an uncharged base containing fluorine can be produced here by a simple deprotonation by means of a base, preferably by means of carbonate, said base containing fluorine subsequently in turn resulting in alternative surfactants containing fluorine with an acid in high yields. The yields over all the synthesis steps are here typically above 90%.

Figure 4:
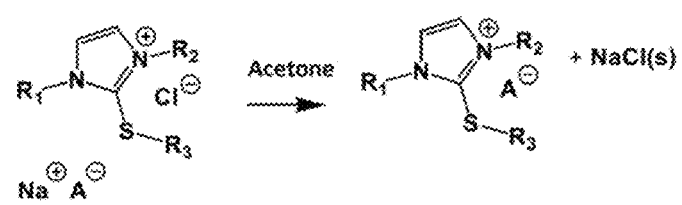
FIG. 4: a schematic reaction equation for the synthesis of a surfactant containing fluorine by metathesis.

FIG. 4 shows a metathesis reaction of a surfactant containing fluorine in accordance with the invention. The designation Cat* stands for a cation here. A preferred metathesis is, for example, represented by the precipitation of sodium chloride in acetone with a simultaneous formation of a new fluorosurfactant.

Figure 5:
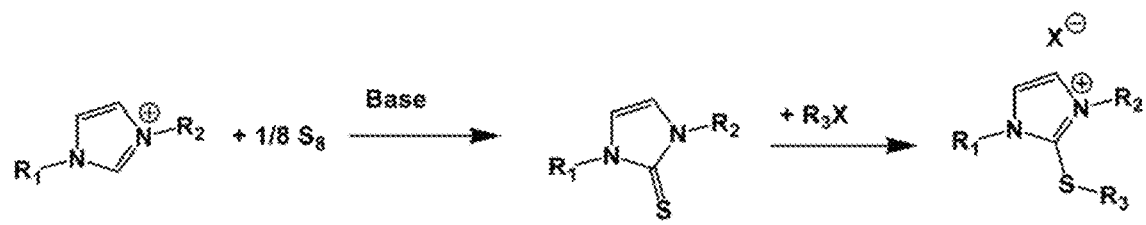
FIG. 5: a reaction equation for the synthesis of a surfactant containing fluorine by thionisation and alkylation.

FIG. 5 describes a general synthetic access to surfactants in accordance with the invention from disubstituted imidazole as the pre-stage.

It must generally be noted that protonated surfactants in accordance with the invention can be deprotonated again in dependence on the pH. This can be used in a targeted manner in some applications. In contrast, disubstituted fluorosurfactants in accordance with the invention are also relatively stable with a basic pH. Under extreme pH conditions, a beta-H elimination can take place in the dialkylated systems and thereupon an elimination of e.g. 1,H,1H,2H,2H-perfluorooct-1-ene. This can promote or facilitate a degradation in certain cases. The cationic charge can be used in a targeted manner here to filter waste waters, for example via ion exchangers, preferably in an acidic or neutral milieu. The above-named degradation reaction can subsequently be used to achieve a removal of the fluorine side chain. This enables a particularly environmentally compatible process.

Figure 6:
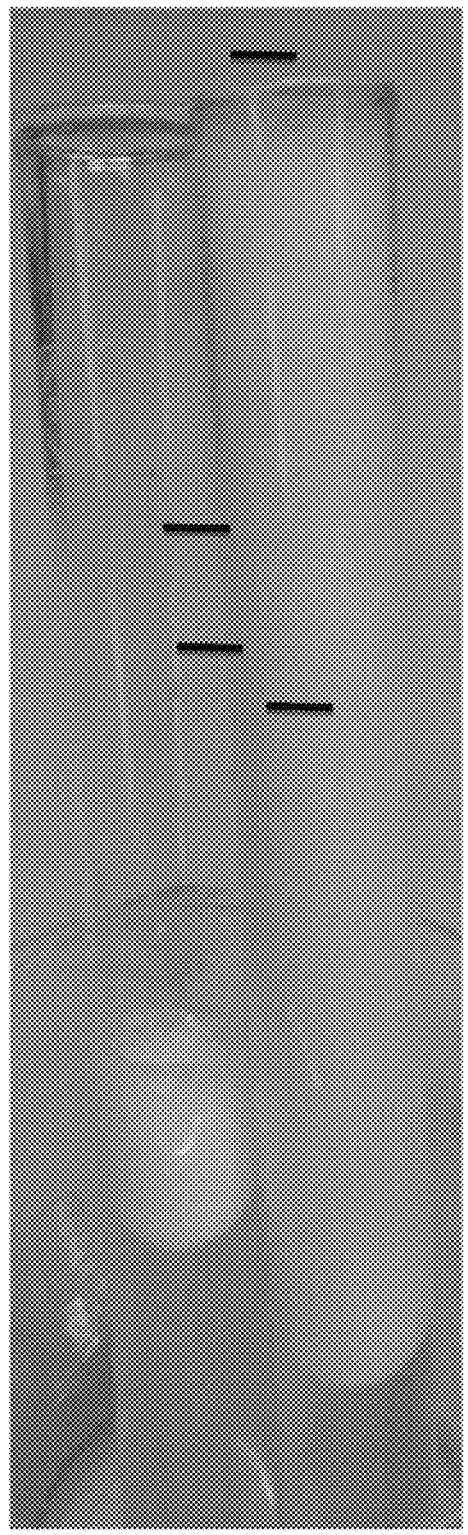
FIG. 6: a photographic image that shows the foam-inhibiting effect of 1-methyl-2-((perfluorohexylethyl)thio) imidazolium-O,S-dimethyl phosphorothioate.

The image in accordance with FIG. 6 is based on the use of the 1-methyl-2-((perfluorohexylethyl)thio)imidazoliumO,S-dimethylphosphorothioate described in synthesis example 5 described below as a defoaming agent. Water and a commercial soap were mixed in equal amounts in both test tubes for the taking of this photograph. The fluorosurfactant in accordance with the invention was subsequently added to the left test tube. Both test tubes were then shaken for 1 minute. The photograph was taken after the test tubes had rested for 10 seconds. The inhibition of the foaming by the surfactant in accordance with the invention can be easily recognized.

Figure 7:
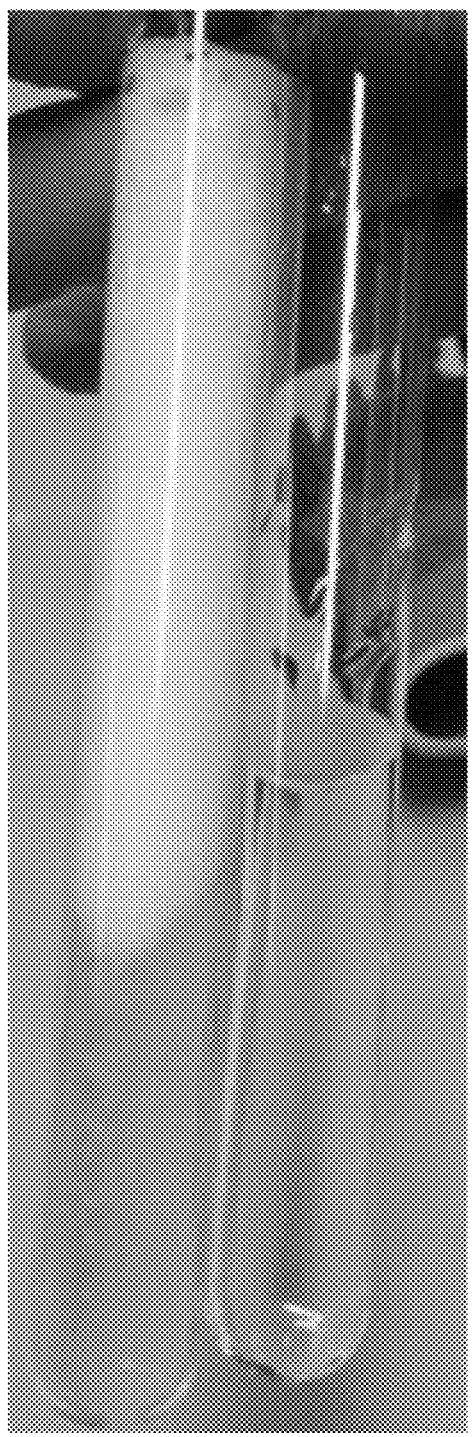
FIG. 7: a photographic image that shows the foam-generating effect of 3-(1-methyl-2-((1H,1H,2H,2H-perfluorooctyl)thio)imidazolium-3-yl) propane-1-sulfonate.

FIG. 7 shows a photograph in which a test tube can be seen on the left that is filled with 10 ml water in which 20 mg 3-(1-methyl-2-((1H,1H,2H,2H-perfluorooctyl)thio)imidazolium-3-yl) propane-1-sulfonate has been dissolved. A test tube having distilled water can be seen on the right. Both test tubes were shaken for 1 minute. A clear foaming due to the surfactant can be observed here.

Figure 8:
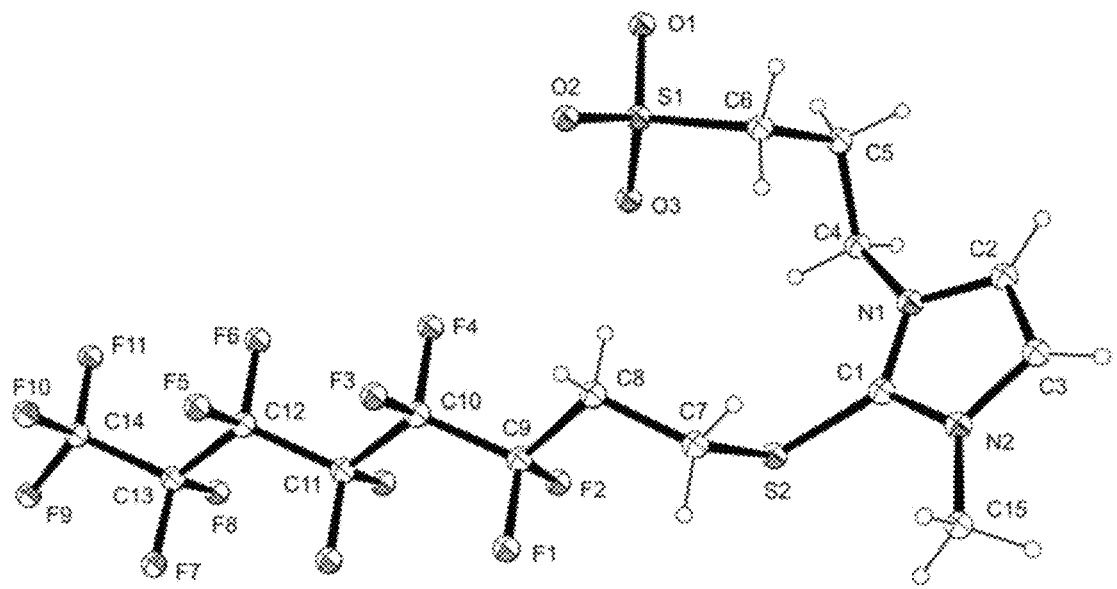
FIG. 8: a representation of the crystal structure of 3-(1-methyl-2-((perfluorohexylethyl)thio)imidazolium-3-yl)propane-1-sulfonate.

FIG. 8 shows the molecular structure determined from single crystal X-ray structure analysis of the fluorosurfactant in accordance with the invention used for taking the photograph of FIG. 7.

Figure 9:
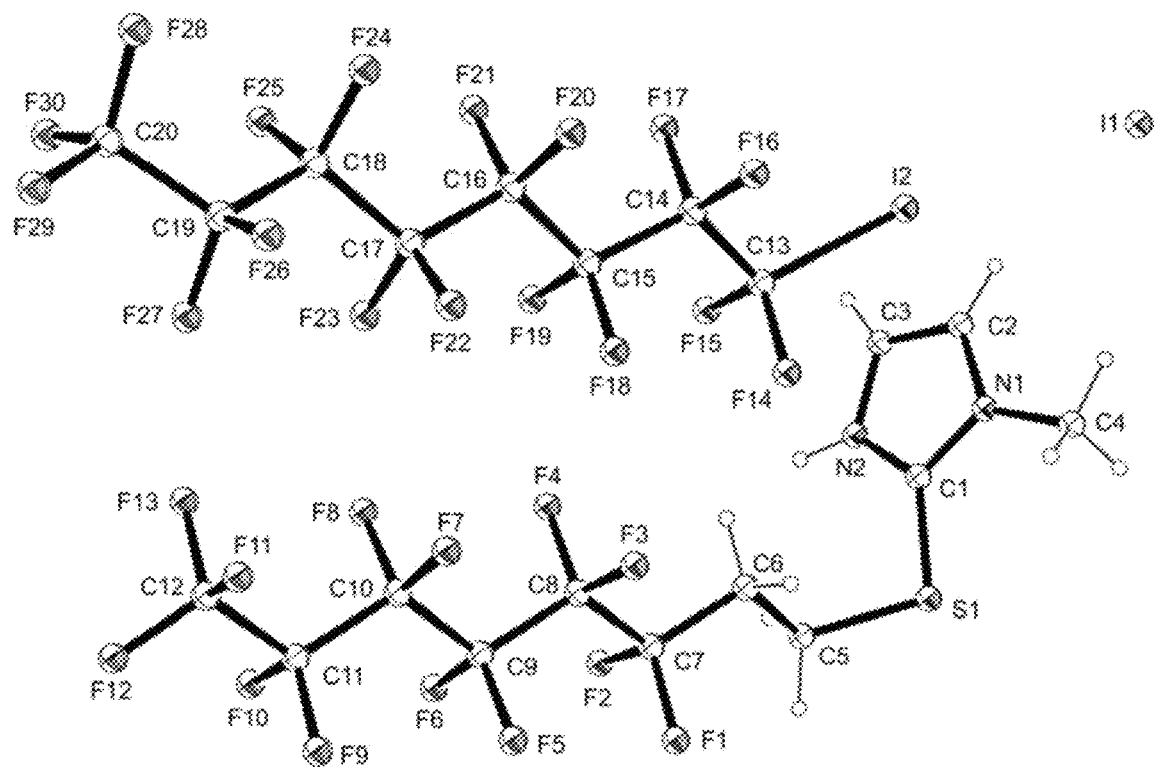
FIG. 9: a representation of the crystal structure of 1-methyl-2-((perfluorohexylethyl)thio)imidazoliumiodide-Co-1-iodoperfluorooctylane.

FIG. 9 shows a halogen complex between a fluorosurfactant in accordance with the invention and 1-iodoperfluorooctane.

SYNTHESIS EXAMPLE 1

Synthesis of 1-methyl-2-((1H,1H,2H,2H-perfluorooctyl)thio)-1H-imidazolium-2-(methacryloyloxy) ethane-1-sulfonate

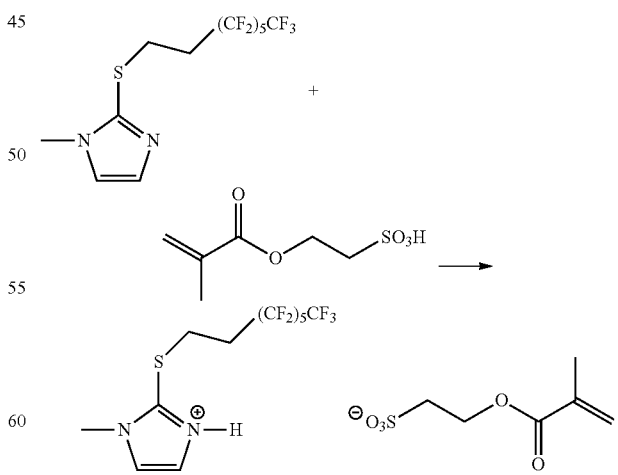

Formulation:
3.067 g (6.66 mmol) 1-methyl-2-((1H, 1H, 2H, 2H-perfluorooctyl)thio)-1H-imidazole 1.267 g (6.52 mmol) 2-methacryloylethane-1-sulfonic acid Performance:

3.067 g (6.66 mmol) 1-methyl-2-((1H, 1H, 2H, 2H-perfluorooctyl)thio)-1H-imidazole and 1.267 g (6.52 mmol) 2-methacrylamidoethane-1-sulfonic acid were admixed without solvent; an immediate reaction and precipitation of the product occurred in this process. The mixture was dissolved in 20 ml methanol in an ultrasound bath for a complete conversion. The solvent was removed at the rotary evaporator. The liquid product was washed with ether, with a white powder being precipitated that was filtered and washed three times with ether.

Yield:

3.867 g 1-methyl-2-((1H,1H,2H,2H-perfluorooctyl)thio)-1H-imidazolium-2-(methacryloyloxy)ethane-1-sulfonate (5.91 mmol, 90.5%)

$^1$H-NMR (300 MHz; 25° C.; CD$_3$OD):

7.73 (I=1; d (J3=3 Hz); CH-imidazolium); 7.69 (I=1; d (J3=3 Hz); CH-imidazolium); 6.12 (I=1; m; CH$_2$=Trans); 5.61 (I=1; m; CH$_2$=cis); 4.49 (I=2; t; CH$_2$—S); 3.96 (3H; s; CH$_3$—N); 3.43 (I=2; t; CH$_2$—NH); 3.17 (I=2; t; CH$_2$—SO$_3$—); 2.68 (I=2; m; CH$_2$—CF$_2$); 1.92 (I=3; m; CH$_3$—C);

$^{13}$C-NMR (75 MHz; 25° C.; CD$_3$OD):

168.71 (C=O); 140.94° C.=); 137.71 (C—S); 127.35 (CH—N); 126.57 (CH$_2$=); 122.70 (CH—N); 61.73 (CH$_2$—SO$_3$$^-$); 51.33 (CH$_2$—N); 36.18 (CH$_3$—N); 32.65 (t; CH$_2$—CF$_2$); 27.76 (t; CH$_2$—S); 18.51 (CH$_3$);

Melting point: 88.6-89.9° C.

Determining the Solubility:

3.84 g 1-methyl-2-((1H, 1H,2H,2H-perfluorooctyl)thio)-1H-imidazolium-2-(methacryloyloxy)ethane-1-sulfonate was added to 5 ml water. The suspension was added to the ultrasound bath for 5 minutes and was centrifuged for 20 minutes. The supernatant was then weighed and was rinsed with argon for 5 minutes to remove any possibly dissolved oxygen. The aqueous, slightly yellow solution weighed 7.126 g. The experiment was performed at approximately 23° C.

A solubility of approximately 430 g/L water results from these data.

SYNTHESIS EXAMPLE 2

Synthesis of 1-methyl-2-((1H,1H,2H,2H-perfluorooctyl)thio)-1H-imidazolium-2-acrylamido-2-methylpropanesulfonate Theoretical Yield:

2.67 g of 1-methyl-2-((1H,1H,2H,2H-perfluorooctyl)thio)-1H-imidazolium-2-acrylamido-2-methylpropanesulfonate.

Performance:

0.829 g (4 mmol) 2-acrylamido-2-methylpropanesulfonic acid were dissolved in 30 ml methanol and 1.841 g (4 mmol) 1-methyl-2-((1H, 1H, 2H, 2H-perfluorooctyl)thio)-1H-imidazol were slowly dripped into 10 ml methanol after 10 minutes of stirring. The mixture was stirred at room temperature for one day and the methanol was subsequently partially removed at the rotary evaporator. Washing with hexane then took place twice; the hexane phase was decanted and the residual solvent was subsequently removed at the rotary evaporator. A white, slightly yellowish product was obtained.

Yield:

2.24 g (83.9% of the theoretical yield)

Evaluation and Characterization $^1$H NMR (300 MHz, CD$_3$OD) δ 7.75 (I=1; d, CH-imidazolium), 7.70 (I=1; d, CH-imidazolium), 6.25 to 6.07 (I=2; m; Trans-CH$_2$= and CH—C=O), 5.58 and 5.55 (I=1; d×d; Cis-CH$_2$=), 3.96 (I=3; s; CH$_3$—N), 3.44 (I=2, t, CH$_2$—S), 3.24 (I=2, s, C—CH$_2$—SO$_3$), 2.78 to 2.60 (I=2, m, CH$_2$—CF$_2$), 1.57 (I=6, s, 2×CH$_3$).

$^{13}$C NMR (75 MHz, CD$_3$OD) δ 167.56 (C=O), 140.93 (C2), 133.69 (CH-vinyl), 127.35 (CH$_2$-vinyl), 125.73 (CH-imidazolium), 122.68 (CH-imidazolium), 60.28 (CH$_2$—SO$_3$), 53.60 (CH$_2$-amide), 36.21 (CH$_3$—N), 32.63 ("txt", CH$_2$—CF$_2$), 27.78 ("t", 27.72 CH$_2$—S), 27.19 (2×CH$_3$).

This surfactant is polymerizable and soluble in water.

Use of Teflon as an Emulsifying Agent:

A solution of 10 ml water, 0.100 g 1-methyl-2-((1H,1H,2H,2H-perfluorooctyl)thio)-1H-imidazolium-2-acrylamido-2-methylpropanesulfonate was dissolved in 10 ml water and 0.200 g Teflon 1 μm (Sigmal-Aldrich) were subsequently added to this solution. A suspension was formed in this process that remained stable for at least 4 hours. After 2 days a white powder had been deposited on the bottom.

SYNTHESIS EXAMPLE 3

Synthesis of 1-methyl-2-((1H,1H,2H,2H-perfluorooctyl)thio)imidazoliumiodide

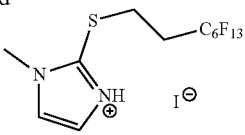

100 g (0.876 mol) 1-methyl-1,3-dihydro-2H-imidazol-2-thion (thiamazole) and 500 g (1.05 mol) 1H,1H,2H,2H-perfluorooctyliodide were dissolved in 500 ml ethanol while heating slightly; the resulting reaction mixture was subsequently refluxed for 36 hours. The solution was then concentrated by means of a rotary evaporator for so long until excessive foaming makes a further concentration a lot more difficult. This saturated solution was then stored overnight at room temperature to allow the product to crystallize. To complete the precipitation of the product and to remove excessive 1H,1H,2H,2H-perfluorooctyliodide, 50 ml diethyl ether were added to the precipitated product. The mixture was shaken for some minutes; the product was then filtered and washed with a further 300 ml diethyl ether; the drying of the product took place for 24 hours in a high vacuum. 500 g of 1-methyl-2-((1H,1H,2H,2H-perfluorooctyl)thio)imidazoliumiodide were then isolated (97% of the theoretical yield).

$^{13}$C NMR (75 MHz, CDCl$_3$) δ 140.65 (s, C(1)), 124.58 (s, C(3)), 121.72 (s, C(2)), 126-100 (m, perfluorohexyl), 36.21 (s, C(4)), 31.39 (t, C(6)), 27.88 (t, C(5)).

$^1$H NMR (300 MHz, CDCl$_3$) δ 10.81 (1H, s(br), NH imidazolium, Note: the chemical displacement of this signal appears to be greatly dependent on the concentration), 7.50 (1H, d, C(3)H imidazolium), 7.44 (1H, d, C(2)H imidazolium), 3.91 (3H, s, CH$_3$), 3.76 (2H, t, CH$_2$—S), 2.61 (2H, tt, CH$_2$—CF$_2$).

Solubility in MeOH: 1300 g/l
Solubility in DMSO: 740 g/l
Solubility in 3M™ Novec™ 71 IPA: 9.6 g/l
Solubility in 3M™ Novec™ 71 IPA as 1-iodoperfluorooctyl-Co-complex: 20.5 g/l

SYNTHESIS EXAMPLE 4

Synthesis of 1-methyl-2-((1H,1H,2H,2H-perfluorooctyl)thio)imidazolium-hexafluoroacetylacetonate

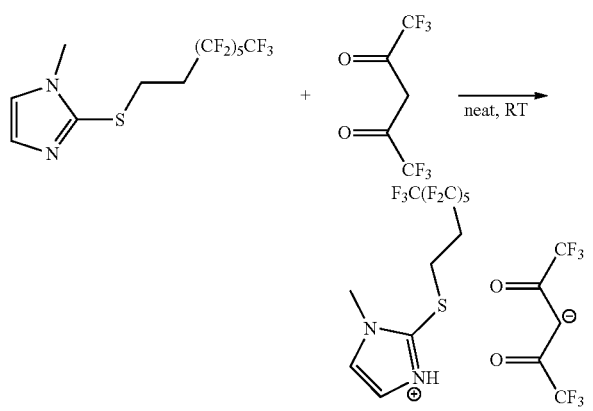

1.04 g (5.0 mmol) hexafluoroacetylacetone were dropped into 2.30 g (5.0 mmol) 1-methyl-2-((perfluorohexylethyl)thio)imidazole; the resulting reaction mixture was then shaken lightly for 2 minutes. The product represents a somewhat viscous, colorless liquid; the yield is quantitative.

$^{13}$C NMR (75 MHz, acetone-d6) δ 174.32 (q, carbonyl-C hexafluoroacetylacetonate), 139.24 (s, C(1)), 124.34 (s, C(3)), 122.92 (s, C(2)), 118.18 (q, CF$_3$ hexafluoroacetylacetonate), 126-100 (m, perfluorohexyl), 85.64 (s(br), carbanion hexafluoroacetylacetonate), 34.27 (s, C(4)), 31.22 (t, C(6)), 26.32 (t, C(5)).

$^1$H NMR (300 MHz, acetone-d6) δ 15.83 (1H, s(broad), NH imidazolium), 7.63 (1H, d, C(3)H imidazolium), 7.40 (1H, d, C(2)H imidazolium), 5.85 (1H, s(broad), CH hexafluoroacetylacetonate), 3.87 (3H, s, CH$_3$), 3.55 (2H, t, CH$_2$—S), 2.59 (2H, tt, CH$_2$—CF$_2$).

SYNTHESIS EXAMPLE 5

Synthesis of 1-methyl-2-((1H,1H,2H,2H-perfluorooctyl)thio)imidazolium-O,S-dimethylphosphorothioate

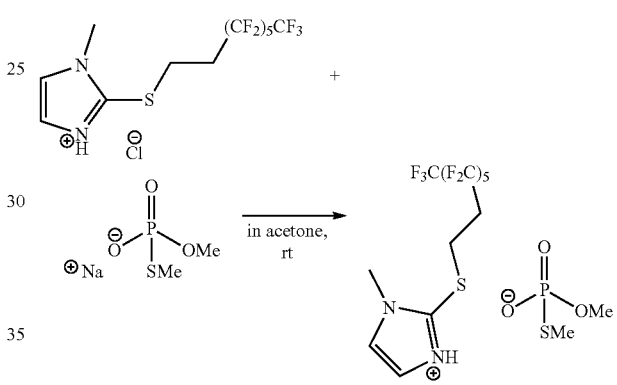

A solution of 0.821 g (5.0 mmol) sodium-O,S-dimethylphosphorothioate in 25 ml acetone was dripped into a dispersion of 2.48 g (5.0 mmol) 1-methyl-2-((1H,1H,2H,2H-perfluorooctyl)thio)imidazoliumchloride in 25 ml acetone while stirring. The resulting reaction mixture was stirred overnight at room temperature; the arising sodium chloride was subsequently filtered. The solvent of the filtrate was removed in the rotary evaporator; a colorless, viscous oil remained. It was dried overnight in a high vacuum; 2.86 g 1-methyl-2-((1H,1H,2H,2H-perfluorooctyl)thio)imidazolium-O,S-dimethyl phosphorothioate resulted (95% of the theoretical yield).

$^{13}$C NMR (75 MHz, acetone-d6) δ 139.73 (s, C(1)), 126.11 (s, C(3)), 124.20 (s, C(2)), 126-100 (m, perfluorohexyl), 52.71 (d, O—CH$_3$ O,S-dimethylphosphorothioate), 35.27 (s, C(4)), 32.05 (t, C(6)), 26.62 (t, C(5)), 12.55 (s, S—CH$_3$ O,S-dimethylphosphorothioate).

$^1$H NMR (300 MHz, acetone-d6) δ 12.31 (1H, s(broad), NH imidazolium), 7.79 (1H, d, C(3)H imidazolium), 7.49 (1H, d, C(2)H imidazolium), 3.93 (3H, s, CH$_3$), 3.56 (5H, apparently s(br), CH$_2$—S and O—CH$_3$ O,S-dimethylphosphorothioate), 2.71 (2H, tt, CH$_2$—CF$_2$), 2.16 (3H, s, S—CH$_3$ O,S-dimethylphosphorothioate).

This compound was added to a solution of water and commercially available soap. A test tube with water and soap without surfactant was used as a reference. Both test tubes were shaken for 1 minute and were photographed after 10 seconds (FIG. 6). It can be observed here that much less foam was formed by the fluorosurfactant.

SYNTHESIS EXAMPLE 6

Synthesis of 3-(1-methyl-2-((1H,1H,2H,2H-perfluorooctyl)thio)imidazolium-3-yl) propane-1-sulfonate

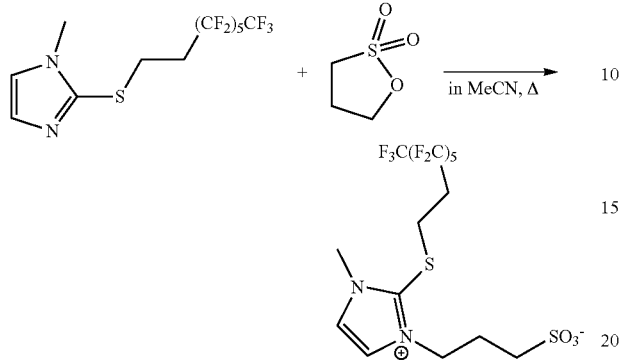

3 g (6.52 mmol) 3-(1-methyl-2-((1H,1H,2H,2H-perfluorooctyl)thio)imidazol and 0.92 g (7.5 mmol) 1,3-propane sultone were dissolved in 5 ml acetonitrile and were refluxed for 16 hours, with a certain amount of product already being precipitated during this time. After cooling the reaction mixture, the precipitation of the product was completed by addition of 50 ml diethyl ether and storing the mixture at −20° C. for some hours. The product was subsequently filtered and washed twice with 30 ml diethyl ether in each case; it was then dried overnight at high vacuum. 3.56 g of white, powdery product were able to be isolated (94% of the theoretical yield).

$^{13}$C NMR (75 MHz, CD$_3$OD) δ 140.66 (s, C(1)), 127.14 (s, C(3)), 125.63 (s, C(2)), 126-100 (m, perfluorohexyl), 49.70 (s, C(6)), 48.66 (s, C(4)), 37.06 (s, C(15)), 32.04 (t, C(8)), 27.96 (t, C(7)), 27.13 (s, C(5))).

$^1$H NMR (300 MHz, CD$_3$OD) δ 8.00 (1H, d, C(3)H imidazolium), 7.89 (1H, d, C(2)H imidazolium), 4.65 (2H, t, C(4)H$_2$), 4.09 (3H, s, CH$_3$), 3.41 (2H, t, CH$_2$—S), 2.93 (2H, t, C(6)H$_2$), 2.79 (2H, tt, CH$_2$—CF$_2$), 2.39 (2H, quin, C(5)H$_2$).

The water solubility amounts to approximately 160 g/l.

Approximately 20 mg of this compound was added to 10 ml water. A test tube with water and without surfactant was used as a reference. Both test tubes were shaken for 1 minute and were photographed after 10 seconds (FIG. 7). It can be observed in this process that this fluorosurfactant is active as a foam forming agent.

SYNTHESIS EXAMPLE 7

Synthesis of 3-((3-octyl-1-(1H,1H,2H,2H-perfluorooctyl)imidazolium-2-yl)thio)propane-1-sulfonate

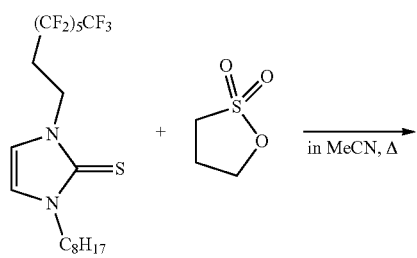

-continued

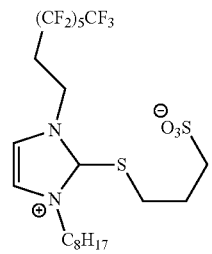

55.8 g (100 mmol) 3-octyl-1-(1H,1H,2H,2H-perfluorooctyl)-1,3-dihydro-2H-imidazol-2-thion and 15.9 g (130 mmol) 1,3-propane sultone were admixed with 65 ml acetonitrile and were carefully refluxed for 16 hours (high foam formation). After cooling the reaction mixture, 300 ml diethyl ether were added for the product precipitation and this mixture was then stored overnight at −20° C. The product was subsequently filtered and washed twice with 150 ml diethyl ether in each case; it was then dried at high vacuum for 24 hours. 37.5 g of white, powdery product resulted (55% of the theoretical yield).

$^{13}$C NMR (75 MHz, CD$_3$OD) δ 141.51 (s, C(1)), 125.96 (s, C(3)), 125.89 (s, C(2)), 126-100 (m, perfluorohexyl), 51.23 (s, C(4)), 50.36 (s, C(22)), 43.15 (t, C(12)), 36.56 (s, C(20)), 32.85 (s, C(5)), 31.61 (t, C(13)), 31.07 (s, C(6)), 30.21 (s, C(7)), 30.10 (s, C(8)), 27.24 (s, C(9)), 27.00 (s, C(21)), 23.64 (s, C(10)), 14.34 (s, C(11))).

$^1$H NMR (300 MHz, CD$_3$OD) δ 8.06 (1H, d, C(3)H imidazolium), 7.98 (1H, C(2)H imidazolium), 4.82 (2H, t, C(124)H$_2$—N), 4.43 (2H, t, C(4)H$_2$—N), 3.29 (2H, t, C(20)H$_2$—S), 3.01 (2H, tt, CH$_2$—CF$_2$), 2.91 (2H, t, C(22)H$_2$—SO$_3$), 2.09 (2H, quin, C(5)H$_2$), 1.93 (2H, quin, C(21)H$_2$), 1.33 (10H, m, C(6-10)H$_2$), 0.89 (3H, t, C(11)H$_3$).

Values for the solubility of the product in different solvents are shown in the following Table 1.

TABLE 1

| Solvent | Solubility (g/l) |
|---|---|
| Et$_2$O | 0.5 |
| Acetone | 3.0 |
| MeCN | 9.0 |
| EtOH | 163 |
| H$_2$O | 2.0 |

EXAMPLE 8

Measurement of Surface Tensions:

The surface tension was determined at suspended drop using a "Drop Shape Analyser DSA 25" of the Krüss corporation. The drop volume at most measurements amounted to approximately 5 µl. The measurements were performed at temperatures between 24.5 and 25.1° C. and at a relative humidity of approximately 19%. Each sample was measured a total of ten times. The standard deviations are marked by s in the table shown below. In the measurements at a concentration of 0.05 wt % surfactant, larger drop volumes were used in some cases to obtain a better reproducibility of the measurement results. The measurement values are shown in the following Table 2.

TABLE 2

|  | Concentration of surfactant in water 0.5 wt % | | Concentration of surfactant in water 0.05 wt % | |
| --- | --- | --- | --- | --- |
|  | n = 10 OFS (mN/m) | s | n = 10 OFS (mN/m) | s |
| 1-methyl-2-((1H,1H,2H,2H-perfluorooctyl)thio)-1H-imidazolium-2-(methacryloyloxy)ethane-1-sulfonate | 16.22 | 0.05 | 23.24 | 0.21 |
| 3-(1-methyl-2-((perfluorohexyl-ethyl)thio)-imidazolium-3-yl)-propane-1-sulfonate | 24.94 | 0.09 | 29.74* | 0.16 |
| Perfluorooctanoic acid | 16 | 0.34 | 55.68** | 0.26 |
| Ammonium-4,8-dioxa-3H-perfluorononanoate | 46.42 | 0.29 | 64.87** | 0.07 |
| 1-methyl-2-((1H,1H,2H,2H-perfluorooctyl)thio)-1H-imidazolium-methanesulfonate | 16.21 | 0.06 | 24.39 | 0.14 |

*Sample volume was 8 μl;
**Sample volume was 20 μl.

Even further measurements of the surface tension were carried out for 1-methyl-2-((1H,1H,2H,2H-perfluorooctyl)thio)-1H-imidazolium-2-(methacryloyloxy)ethane-1-sulfonate in different concentrations in accordance with the same method as described above. The result is collected in Table 3 below.

TABLE 3

| c (%) | OFS (mN/m) | s |
| --- | --- | --- |
| 0.5 | 16.22 | 0.05 |
| 0.1 | 20.8 | 0.09 |
| 0.05 | 23.24 | 0.21 |
| 0.01 | 32.11 | 0.29 |
| 0.005 | 70.28 | 0.2 |

At a concentration of 0.5 wt % in water, the values of the surfactants in accordance with the invention are comparable with the prior art. At lower surfactant concentrations, this is, however, easily exceeded. In addition, 1-methyl-2-((1H,1H,2H,2H-perfluorooctyl)thio)-1H-imidazolium-2-(methacryloyloxy)ethane-1-sulfonate can still be polymerized, which can, for example in lacquers, result in an additionally increased environmental compatibility.

EXAMPLE 9

Synthesis of Hydrogels

Different hydrogels were synthesized. The starting products are listed in the following Table 4.

TABLE 4

|  | Reference | Hydrogel 1 | Hydrogel 2 | Hydrogel 3 | Hydrogel 4 |
| --- | --- | --- | --- | --- | --- |
| Sodium 2-acrylamido-2-methanepropanesulfonate | 48.00 | 39.18 | 43.20 | 43.20 | 39.18 |
| Water | 48.00 | 39.18 | 43.20 | 43.20 | 39.18 |
| Ethyleneglycoldimethacrylate | 2.96 | 2.42 | 2.66 | 2.66 | 2.42 |
| 2-hydroxy-2-methyl-1-phenyl-1-propanone | 1.04 | 0.85 | 0.94 | 0.94 | 0.85 |
| 3-((1-(1H,1H,2H,2H-perfluorooctyl)-3-vinyl-1H-imidazolium-2-yl)thio)propane-1-sulfonate | — | 18.37 | 10.00 | — | — |
| 1-methyl-2-((1H,1H,2H,2H-perfluorooctyl)thio)-1H-imidazolium 2-acrylamido-2-methylpropane sulfonate | — | — | — | 10.00 | 20.00 |
| Weighted sample [g] | 2.72 | 2.64 | 2.29 | 2.26 | 3.65 |
| Swollen for 13 hours in 800 ml water | 77.69 | 21.72 | 27.59 | 32.26 | 47.55 |
| Ratio | 28.56 | 8.23 | 12.05 | 14.27 | 13.03 |
|  | Transparent | Transparent | Transparent | Opaque | White |

The examples show that the fluorosurfactants used are suitable for installation in a hydrogel. The swell behavior was furthermore changed in this process, but remained surprisingly high despite a high fluorine content. Hydrogels 1 and 2, that still remained transparent despite the high water absorption, are above all worthy of note. This could in particular be of advantage in contact lenses. With a high fluorine content in hydrogels, the refractive index of the hydrogel, on the one hand, and the oxygen solubility or oxygen permeability, on the other hand, can be modified in a targeted manner.

The fluorosurfactants in accordance with the invention are inter alia also intended for use in an aqueous medium. A good water solubility can be of great interest here. Some of the compositions in accordance with the invention showed a surprisingly high water solubility in this process. Table 5 shown below comprises some measured values. The values are not exact and only serve a better understanding.

TABLE 5

| Substance | Solubility in water [g/l] |
| --- | --- |
| 1-methyl-2-((1H,1H,2H,2H-perfluorooctyl)thio)imidazoliumchloride | 1750 |
| 1-methyl-2-((1H,1H,2H,2H-perfluorooctyl)thio)imidazoliumbromide | 1200 |
| 1-methyl-2-((1H,1H,2H,2H-perfluorooctyl)thio)imidazoliumiodide | <1 |
| 3-(1-methyl-2-((1H,1H,2H,2H-perfluorooctyl)thio)imidazolium-3-yl) propane-1-sulfonate | 160 |
| 3-((3-octyl-1-(1H,1H,2H,2H-perfluorooctyl)imidazolium-2-yl)thio)propane-1-sulfonate | 2 |
| 1-methyl-2-((1H,1H,2H,2H-perfluorooctyl)thio)imidazolium-(±)-camphor-10-sulfonate | >4000 |

A high viscosity gel that, however, had no visible solid residue was formed in some compounds.

Further experiments showed that the fluorosurfactants in accordance with the invention can also be worked into sticky compositions such as in sticky hydrogels and that an adhesion to different substrates such as steel or the human skin is still achieved.

EXAMPLE 10

Determining the Surface Tension

The determination of the static surface tension for 3-(1H,1H,2H,2H-perfluorooctyl)-2-((1H,1H,2H,2H-perfluorooctyl)thio)-1-methyl-1H-imidazolium chloride in water produced the values indicated in the following Table 6 for the surface tension (OFS) in nN/m at different concentrations c in wt %. The values for OFS represent the mean value from 10 measurements. The standard deviation S [mN/m] for these values is likewise indicated.

TABLE 6

| c (wt %) | OFS (mN/m) | S [mN/m] |
|---|---|---|
| 0.5000 | 14.5 | 0.04 |
| 0.2500 | 15.5 | 0.04 |
| 0.1000 | 15 | 0.1 |
| 0.0750 | 15.02 | 0.05 |
| 0.0500 | 15.05 | 0.04 |
| 0.0250 | 14.43 | 0.03 |
| 0.0100 | 16.29 | 0.04 |
| 0.0075 | 18.89 | 0.05 |
| 0.0050 | 21.29 | 0.05 |
| 0.0025 | 40.74 | 0.4 |

The measurement values show that the surface tension of water considerably drops on the addition of the surfactant, with the surfactant itself still showing a large effect at very small concentrations.

EXAMPLE 11

Fluorosurfactant for Use as a Ski Wax 95 g of a paraffin wax were melted at 150° and 5 g 1-octyl-3-(1H,1H,2H,2H-perfluorooctyl)-2-((1H,1H,2H,2H-perfluorooctyl)thio)-1H-imidazoliumiodide were added. The mixture was intensely stirred until a homogeneous melt was able to be recognized. The melt was brought to solidification by cooling to room temperature.

The wax mixture thus obtained was applied to the running surface of a cross-country ski using an iron. The sliding properties of this ski were compared with the sliding properties of a ski treated with the pure paraffin wax under spring-like snow conditions. The ski treated with a wax in accordance with the invention showed considerably better sliding properties.

EXAMPLE 12

Fluorosurfactant for Use as a Foam Forming Agent

The components listed in the following Table 7 were mixed and the mixture was shaken in the ultrasound bath until homogeneity.

TABLE 7

| Substance | Quantity |
|---|---|
| 3-(1H,1H,2H,2H-perfluorooctyl)-1-vinyl-1H-imidazoliumchloride | 2 g |
| 2,2'-azobis(2-methylpropionamidine)-dihydrochloride | 0.1 g |
| Water | 95.5 g |

The homogeneous mixture obtained was heated to 65° C. to start a polymerization reaction. Cooling took place to room temperature after 6 h. A stable emulsion was obtained. Subsequently, 1.9 g 2-((1H,1H,2H,2H-perfluorooctyl)thio)-1-methyl-1H-imidazoliumchloride and 0.5 g 3-(1H,1H,2H,2H-perfluorooctyl)-2-((1H,1H,2H,2H-perfluorooctyl)thio)-1-methyl-1H-imidazoliumchloride were added and the two components were carefully dissolved in the ultrasound bath.

The mixture thus obtained was characterized by a particularly fast and stable foam formation. This property is significant, for example, in a use in fire extinguishing foams.

The invention claimed is:

1. A composition comprising:
   1) a surfactant having:
      a cationic group,
      a bivalent or polyvalent sulfurous group, and
      a fluorinated group;
   2) an anion corresponding to the cationic group of the surfactant;
   wherein the cationic group is an N-substituted heterocyclic group selected from the group consisting of an N,N-disubstituted imidazolium group, an N,N-disubstituted imidazolinium group, and an N,N-disubstituted benzimidazolium group.

2. The composition in accordance with claim 1, wherein the cationic group is an N,N-disubstituted imidazolium group.

3. The composition in accordance with claim 1, wherein the fluorinated group is a fully fluorinated hydrocarbon group of the type $C_nF_{2n+1}$, where n is 5, 6, or 7.

4. The composition in accordance with claim 1, wherein the sulfurous group is a thioether.

5. The composition in accordance with claim 1, wherein the anion is selected form the group consisting of a fluoride, a chloride, a bromide, an iodide, an aryl sulfonate, an alkyl sulfonate, an alkyl sulfate, a sulfate, an aryl phosphonate, an alkyl phosphonate, a monoalkyl phosphate, a dialkyl phosphate, a (di)hydrogen phosphate, a phosphate, a hexafluorophosphate, a hydrogen carbonate, a carbonate, a carbamate, an alkyl carbonate, a trifluoromethanesulfonate, a bis (trifluoromethane sulfonyl)imide, a nonaflate, and a carboxylate.

6. The composition in accordance with claim 1, wherein the anion is covalently bonded to the surfactant.

7. The composition in accordance with claim 6, wherein the anion is covalently bonded to a nitrogen atom of the cationic group via an interposed spacer.

8. The composition in accordance with claim 7, wherein the spacer is a linear or branched C1-C10 alkylene group.

9. The composition in accordance with claim 7, wherein characterized in that the spacer is a linear or branched C1-C5 alkylene group.

10. The composition in accordance with claim 7, wherein the spacer is an ethylene group.

11. The composition in accordance with claim 6, wherein the anion is covalently bonded to the sulfurous group of the surfactant, either directly or via an interposed spacer.

12. The composition in accordance with claim 1, wherein the fluorinated group is bonded to a nitrogen atom of the cationic group, either directly or via an interposed spacer.

13. The composition in accordance with claim 1, wherein the surfactant has one of the following structures:

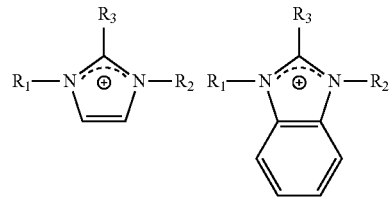

where one of the residues $R_1$, $R_2$ or $R_3$ represents a $(CH_2)_{1-5}(CF_2)_{3-10}CF_3$ group and the two further ones of the residues represent, independently of one another, hydrogen or a linear or branched C1-C10 alkyl group that has a crosslinkable group or is covalently bonded to the anion.

14. The composition in accordance with claim 1, wherein the fluorinated group is covalently bonded to the sulfurous group, either directly or via an interposed spacer.

15. The composition in accordance with claim 1, wherein the fluorinated group is a fully fluorinated and linear group of the type $C_nF_{2n+1}$, wherein n is from 3 to 10.

16. The composition in accordance with claim 1, wherein the fluorinated group is a fully fluorinated and linear group of the type $C_nF_{2n+1}$, wherein n is 5, 6, or 7.

17. A method for altering a property of a solution comprising adding the composition of claim 1 to the solution, wherein said property is surface tension, foaming, an optical property, oxygen solubility or oxygen permeability.

18. A method of preparing a composition in accordance with claim 1, wherein
    said method comprises the step of a conversion of an uncharged compound having an N-alkylated heterocyclic group, a divalent sulfurous group, and a fluorinated group with an acid.

19. A method of preparing a composition in accordance with claim 1, wherein
    the method comprises a metathesis for exchanging the anion corresponding to the cationic group of the surfactant containing fluorine.

* * * * *